US010613072B2

(12) United States Patent
Drenzek et al.

(10) Patent No.: US 10,613,072 B2
(45) Date of Patent: Apr. 7, 2020

(54) ISOTOPE ANALYSIS

(71) Applicant: Elementar UK Ltd., Cheadle (GB)

(72) Inventors: Nicholas Drenzek, Cheadle (GB);
Robert Panetta, Cheadle (GB); Kyle Taylor, Cheadle (GB)

(73) Assignee: Elementar UK Ltd., Cheadle (GB)

( * ) Notice: Subject to any disclaimer, the term of this patent is extended or adjusted under 35 U.S.C. 154(b) by 150 days.

(21) Appl. No.: 15/626,377

(22) Filed: Jun. 19, 2017

(65) Prior Publication Data

US 2017/0284993 A1 Oct. 5, 2017

Related U.S. Application Data

(63) Continuation of application No. PCT/GB2015/054084, filed on Dec. 18, 2015.

(30) Foreign Application Priority Data

Dec. 19, 2014 (GB) .................................. 1422734.2

(51) Int. Cl.
*G01N 33/24* (2006.01)
*G01N 31/12* (2006.01)
*H01J 49/04* (2006.01)
*G01N 33/00* (2006.01)
(Continued)

(52) U.S. Cl.
CPC .......... *G01N 33/241* (2013.01); *G01N 33/004* (2013.01); *G01N 33/0042* (2013.01); *G01N 33/0044* (2013.01); *H01J 49/0422* (2013.01); *G01N 5/00* (2013.01); *G01N 21/31* (2013.01); *G01N 31/12* (2013.01)

(58) Field of Classification Search
CPC ............. G01N 33/0037; G01N 33/004; G01N 33/0042; G01N 33/005; G01N 31/12; G01N 33/241

USPC .............................................. 422/80, 78, 119
See application file for complete search history.

(56) References Cited

U.S. PATENT DOCUMENTS 5,440,120 A 8/1995 Roberts et al.
5,661,038 A 8/1997 Brenna et al.
(Continued)

FOREIGN PATENT DOCUMENTS

GB 2271179 A 4/1994
JP 03843184 B2 11/2006
WO 2012016624 A1 2/2012

OTHER PUBLICATIONS

Kamruddin et al., "Thermogravimetry-evolved gas analysis—mass spectrometry system for materials research," Bulletin of Materials Science, vol. 26, No. 4, May 13, 2002 pp. 449-460.
(Continued)

*Primary Examiner* — Lessanework Seifu
(74) *Attorney, Agent, or Firm* — EIP US LLP

(57) ABSTRACT

The invention provides apparatus and methods for determining the isotope ratio of a sample. The apparatus comprises a dynamically heated chamber (1); a reactor (4), wherein an outlet of the dynamically heated chamber is coupled to a reactor inlet; an isotope ratio spectrometer (6), wherein an outlet of the reactor is coupled to a spectrometer inlet; such that a gas flow path is provided from the dynamically heated chamber to the isotope ratio spectrometer; wherein the apparatus includes at least one selective gas trap (3,5) in the gas flow path, the gas trap being configured to selectively and reversibly trap one or more gases present in the gas flow in use.

12 Claims, 1 Drawing Sheet

(51) Int. Cl.
    *G01N 5/00*     (2006.01)
    *G01N 21/31*     (2006.01)

(56) References Cited

U.S. PATENT DOCUMENTS

| | | |
|---|---|---|
| 2007/0178011 A1 | 8/2007 | Elrod et al. |
| 2011/0201126 A1 | 8/2011 | Hughes |

OTHER PUBLICATIONS

Lopez-Capel et al., "Coupling of Thermal analysis with quadrupole mass spectrometry and isotope ratio mass spectrometry for simultaneous determination of evolved gases and their carbon isotopic composition," Journal of Analytical and Applied Pyrolysis, vol. 75, No. 2, Mar. 1, 2006 pp. 82-89.

David C Manning et al., "Carbon ispotope determination for separate components of heterogeneous materials using coupled thermogravimetric analysis/isotope ratio mass spectrometry," Rapid Communications in Mass Spectrometry, vol. 22, No. 8, Apr. 30, 2008, pp. 1187-1195, GB.

Francois Fourel et al., "18O/16O ratio measurements of inorganic and organic materials by elemental analysis-pyrolysis-isotope ratio mass spectrometry continous-flow techniques," Rapid Communications in Mass Spectrometry, vol. 25, No. 19, Oct. 15, 2011, pp. 2691-2696, GB.

Cara J Mulligan et al., "Thermal decomposition of wheat straw and Mallee Residue Under Pyrolysis Conditions +" Energy and Fuels, vol. 24, No. 1 Jan. 21, 2010, pp. 46-52, Washington, DC, US.

Francioso et al., "Thermal analysis (TG-DTA) and isotopic characterization (13C-15N) of humic acids from different origins", Applied Geochemistry, vol. 20, pp. 537-544, Dec. 8, 2003.

Rosa et al., "Direct Detection of Black Carbon in Soils by Py-GC/MS, Carbon-13 NMR Spectroscopy and Thermogravimetric Techniques", Soil Science Society of America, vol. 72: No. 1, pp. 258-267, Jan. 2008.

Kettrupp et al., "Application of combined thermal analysis—mass spectrometry in the analysis of fossil fuels and polymers", Thermochimica Acta, vol. 93, pp. 629-631, Sep. 15, 1985 (Abstract only).

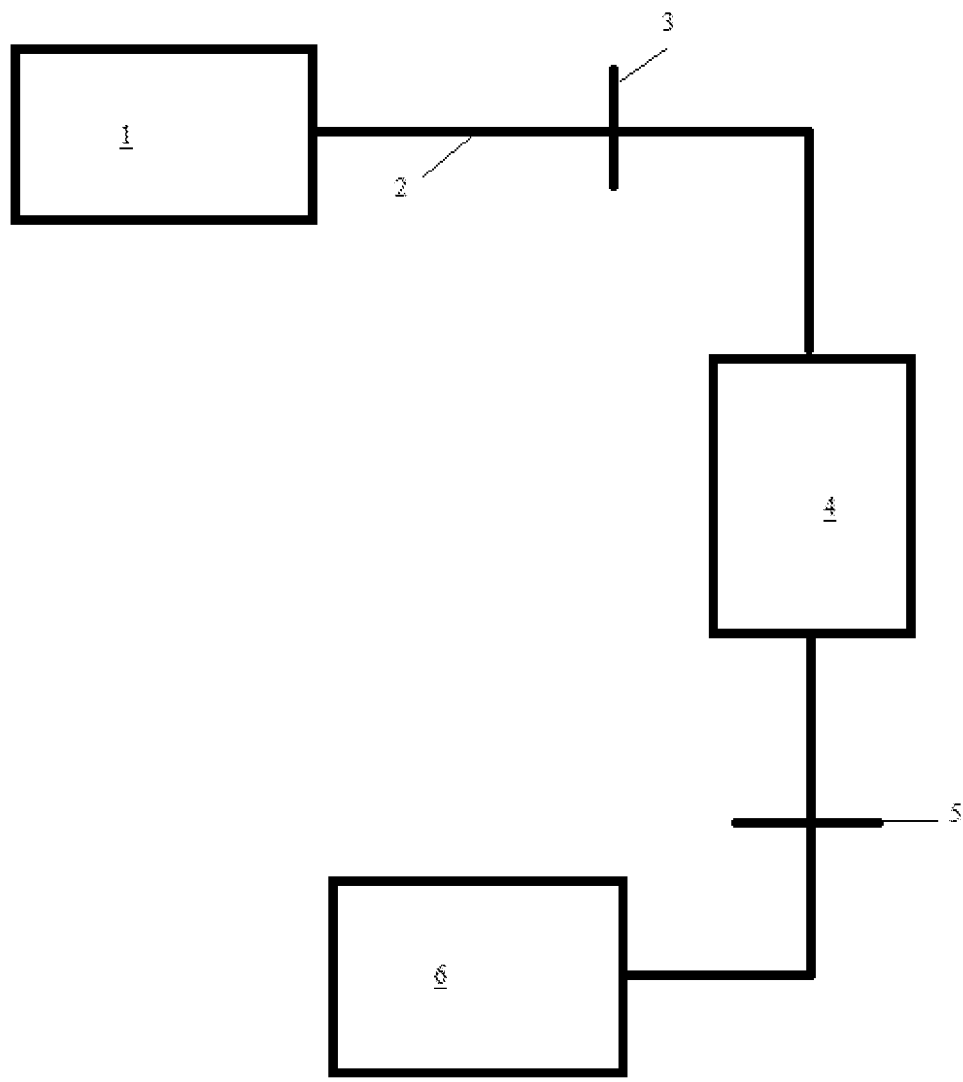

ISOTOPE ANALYSIS

CROSS-REFERENCE TO RELATED APPLICATIONS

This application is a Continuation of International Patent Application No. PCT/GB2015/054084, filed on Dec. 18, 2015, which claims priority to foreign patent application GB 1422734.2, filed on Dec. 19, 2014, the contents of which are hereby incorporated by reference in their entirety.

BACKGROUND OF THE INVENTION

Field of the Invention

The present invention relates to apparatus and methods for analysing isotope ratios.

Description of the Related Technology

Thermogravimetric analysis is a known technique in which the change in physical properties of materials are measured as a function of increasing temperature. Fractions of a sample can be thermally differentiated, allowing the mass of each fraction to be accurately determined and/or allowing the various fractions to be characterised with an additional detector (such as a spectrometer). However, it is not easy to screen the separate fractions to determine their isotopic composition.

It is possible to measure the bulk stable isotope ratios of the total, non-fractionated sample via bulk analytical methods; for example using a combustion/reduction elemental analyser coupled to an isotope ratio mass spectrometer EA-IRMS. Alternatively, the isotope ratios of particular compounds within the sample can be determined via a laborious, low-throughput preparation involving solvent extraction, preparatory chromatography, etc. prior to introduction to a gas chromatograph (GC) interfaced to an isotope ratio mass spectrometer.

Coupling of thermogravimetric analysis (TGA) to isotope ratio mass spectrometers has been described by Manning et al; see for example, J. Anal. Appl. Pyrolysis 75 (2006) 82-89 (the contents of which is included herein by reference). In this paper, lingocellulosic materials are subjected to thermal analysis, forming $CO_2$ which is subsequently subjected to mass spectrometry to determine the $^{13}C$ content.

SUMMARY

At its most general, the invention provides a method and apparatus for performing isotopic analysis of thermally differentiated fractions of a source material. A thermogravimetric analyser (TGA) is coupled to an isotope ratio spectrometer (IRS).

Specifically, in a first aspect, the invention provides apparatus comprising:
  a dynamically heated chamber;
  a reactor, wherein an outlet of the dynamically heated chamber is coupled to a reactor inlet;
  an isotope ratio spectrometer, wherein an outlet of the reactor is coupled to a spectrometer inlet;
  such that a gas flow path is provided from the dynamically heated chamber to the isotope ratio spectrometer,
  wherein the apparatus includes at least one selective gas trap in the gas flow path,
  the gas trap being configured to selectively and reversibly trap one or more gases present in the gas flow in use.

The dynamically heated chamber is used to thermally differentiate/separate fractions of a sample in use. In use, the temperature in the chamber is changed/increased over time while the sample is in the chamber. In some embodiments, the chamber temperature increase may be stepped so that discrete fractions of the sample are released separately. The dynamically heated chamber may be a thermogravimetric analyser. For conciseness, further discussion of the dynamically heated chamber which is used to thermally separate fractions of a sample may simply refer to a thermogravimetric analyser, but the skilled person will recognise that other chambers can be used. Similarly, thermal differentiation of the samples may be referred to as thermogravimetric analysis but the skilled person will recognise that other dynamically heated chambers can be used to perform this process, and that thermal differentiation does not have to be completed with a thermogravimetric analyser.

In some cases, the at least one selective gas trap may be provided between the thermogravimetric analyser and the reactor and/or between the reactor and the spectrometer.

In other words, the at least one selective gas trap may be provided in the gas flow path downstream of the thermogravimetric analyser and upstream of the reactor and/or downstream of the reactor and upstream of the spectrometer. As used herein, the terms "upstream" and "downstream" are terms used to describe the relative position of various components along the gas flow path. The upstream end of the gas flow path is the dynamically heated chamber (or thermogravimetric analyser) and the downstream end of the gas flow path is the isotope ratio spectrometer.

The apparatus as described herein is more versatile than known systems which couple thermogravimetric analysis with isotope ratio spectrometers. In particular, it can be used to determine the natural abundance stable isotope value (i.e., $\delta^{13}C$ and/or $\delta^{34}S$ and/or $\delta D$ and/or $\delta^{15}N$) of thermally differentiated constituents of solid and heavy liquid samples—including, but not limited to, petroleum source and reservoir rocks, kerogen and bitumen isolates, and drill cuttings—as generated by successive volatilization and thermal decomposition. It can also be used to monitor the pyrolysis of such sources.

Suitable analytes for isotope ratio spectroscopy include CO, $CO_2$, $SO_2$, $H_2$ and $N_2$ (In the method aspect of this invention, the analyte is referred to as a reacted gas. The terms are used interchangeably.) The volatilized TGA output from solid and heavy liquid sources cannot generally be introduced directly into an IRS; it must first be processed into one or more of these IRS amenable analytes. Even then, the gas stream cannot generally be introduced directly into the IRS for a number of reasons, including namely:

(1) The ionization sources of mass spectrometers/the sample vessel of spectrometers are typically designed to accept a limited type and amount of non-hydrocarbon (i.e. analyte) gases. The non-hydrocarbon gases in the method utilised herein are quantitative conversion products of organic precursors (whose isotopic compositions cannot be determined through spectroscopic means); the levels of various non-hydrocarbon gases cannot be predicted since that depends on the source material. Careful control of the IRS input is required; if the feed rate is too high, the linear response range of the IRS instrument may be exceeded. Direct transfer of the TGA output gases to the IRS can result in non-linear IRS behaviour and skewed results.

(2) The number of gas species in the TGA output from such samples can results in complex spectra, hindering or preventing accurate analysis.

(3) Simple real-time conversion of the TGA output stream to analysable gases e.g. $CO_2$ and direct transfer of these gases to the IRS inlet may result in mixing of products liberated at various stages of the TGA program, compromising the determination of the isotopic ratios within different fractions.

The inclusion of one or more selective gas traps allows the composition and feed rate of the IRS inlet gas to be selectively controlled whilst maintaining the separation of gases evolved from different fractions.

In some embodiments, there is a first selective gas trap in the gas flow path between the reactor and the spectrometer. This selectively and quantitatively retains the gases to be analysed by the IRS, purifying the IRS analyte and allowing gas flow rate into the IRS to be controlled. A purer analyte provides clearer IRS data, removing other gases that might interfere. The trap ensures good data quality in the event of pressure surges or the like. It also ensures that all of the analyte from a fraction can be collected so that it is subjected to IRS analysis at one time, giving a more accurate IRS reading.

The first selective gas trap may be configured to trap one or more gases selected from carbon dioxide, sulphur dioxide, nitrogen and hydrogen. In one case, it may be configured to trap carbon dioxide. Purification of the IRS $CO_2$ analyte removes other gases which may interfere in the IRS data such as $N_2O$ and $H_2O$ (which give rise to signals that overlap with the $CO_2$ signals in mass spectrometry and spectroscopy respectively). Corresponding effects are seen in relation to other possible analyte gases.

The first selective trap may comprise a sorbent material, selected to specifically trap the analyte gas, whilst allowing other gases to pass through the trap. The sorbent material may adsorb the analyte gas. The sorbent may comprise a metal oxide, a polymer or a molecular sieve of from about 120 to about 28 mesh.

In some embodiments, there is a second selective gas trap in the gas flow path between the thermogravimetric analyser and the reactor. This may be configured to selectively trap volatilized hydrocarbons that are liberated during thermal analysis; non-hydrocarbon gases pass through the trap and are not retained. This purifies the reactor inlet gas, improving the reaction efficiency. It additionally allows the gas flow rate through the apparatus to be controlled, thereby allowing accurate IRS measurement.

The second selective trap may comprise sorbent material that selective traps hydrocarbons whilst allowing non-hydrocarbons to pass through the trap. The sorbent material may adsorb the hydrocarbons. The sorbent material may comprise a metal oxide, a polymer or a molecular sieve of from about 120 to about 28 mesh.

In an alternative embodiment, no second selective trap is employed and all of the TGA output passes directly to the reactor.

In some embodiments, both the first and second selective gas traps are employed. The traps purify the reactor input, increasing reactor efficiency, and purify the IRS analyte, allowing fine control of the IRS input composition and feed rate. In addition, the downstream trap improves data quality in the event that gas release from the upstream trap is uneven or asymmetric.

In these or further embodiments, more than one selective gas trap may be disposed between the reactor and the spectrometer in the flow path. These may be selective for different analytes, thereby allowing the isotopic ratio of different elements to be determined easily. Optionally, these may be linked to the same or separate isotope ratio spectrometers. In an alternative case, the traps may each be selective for the same analyte(s) to improve the trapping efficacy.

Similarly, there may be more than one trap disposed in the flow path between the thermogravimetric analyser and the reactor.

The selective gas traps used may be any type of gas trap known in the art. For example, the gas trap may work by condensation, sorption or other mechanisms. For example, types of suitable gas traps include Tenax TA, Carboxen 572 or Molecular Sieve 5A.

As used herein, "first" and "second" do not denote the number of traps present, but are used simply to denote two traps which differ in location in the gas stream and/or in function. Thus, in one embodiment, only a first trap is included. In another, only the second trap is included. In yet another, both a first and second trap are included.

In some embodiments, one or more of the selective gas traps additionally comprises a heater. The trap(s) can be heated up in use to effect desorption, thereby releasing sorbed gas into the gas flow path. The heater may comprise a resistive wire wound, coiled or helically arranged around the selective gas trap. The heater may be a heated cartridge, around which the trap is coiled. Alternatively, the trap may simply be placed in an oven.

Separation of the thermogravimetric analysis and reaction modules facilitates greater control over the reaction step. The reaction can be finely tuned; for example, (a) a catalyst can be used in a separate reactor module without interfering with the thermogravimetric analysis, and/or (b) the operating conditions can be selected to selectively react components of the TGA output. Such reaction tuning is not easily achieved in prior art disclosures in which the TGA output is oxidised or reduced significantly within the TGA module. Separation of the thermogravimetric analysis and reaction modules also allows a trap to be included in the gas flow path between these modules, offering the advantages discussed above.

In some embodiments, the reactor may comprise a catalyst. In other embodiments, the reactor may include a reagent gas input port, to allow an oxidizing or a reducing reagent gas to be introduced into the reactor and synthesize an oxidation or reducing catalyst within the reaction. The catalyst may catalyse one or more of the following reactions;

(a) oxidation of hydrocarbons and carbon monoxide to carbon dioxide;

(b) oxidation of sulphur-containing compounds to sulphur dioxide;

(c) sequential oxidation-reduction of nitrogen-containing compounds to nitrogen;

(d) reduction of hydrocarbons to hydrogen gas and carbon monoxide; and (e) pyrolysis of hydrocarbons to hydrogen gas.

The catalyst may comprise one or more transition metals or noble metals, such as copper, platinum, nickel, chromium and palladium. The metals may be employed as wires or in powdered form.

The isotope ratio spectrometer may comprise an isotope ratio mass spectrometer (IRMS). Alternatively, it may comprise a spectroscopy-based system, such as cavity ring-down spectroscopy, infrared isotope spectroscopy, integrated cavity output spectroscopy, quantum cascade laser spectroscopy, based apparatus and the like.

The apparatus may also comprise a water removal unit in the gas flow path. A water removal unit may be provided downstream of the reactor; in such cases, it may be provided upstream of the first gas trap (where present). Suitable water removal units include nafion tubing, or other water sorbents such as syncopant.

The thermogravimetric analyser may be a pyrolytic and/or oxidative thermogravimetric analyser. It may be specifically configured for rock analysis. For example, it may be a Weatherford® Source Rock Analyzer (SRA) or a Vinci® Rock-Eval (RE).

In a second aspect, the invention provides a method of determining isotope ratios in fractions of a sample, the method comprising the sequential steps of;

(i) dynamically heating the sample to thermally differentiate fractions of the sample, suitably thermogravimetric analysis;

(iii) reaction of the step (i) output to produce a reacted gas; and (v) completing isotope ratio spectrometry on the reacted gas;

wherein the method additionally comprises;

(ii) selectively and reversibly trapping components of the step (i) output prior to step (iii); and/or (iv) selectively and reversibly trapping components of the reacted gas prior to step (v).

Where step (i) comprises thermogravimetric analysis, the "step (i) output" may be referred to as the thermogravimetric output.

The reaction step may comprise oxidation and/or reduction and/or pyrolysis.

Features described above in relation to the first may be combined with the second aspect, to the extent that such a combination is possible.

Specifically (and as set out above in relation to the first aspect), in some embodiments the method of the invention may comprise steps (i), (ii), (iii) and (v). In other embodiments, it may comprise steps (i), (iii), (iv) and (v). In yet further embodiments, it may comprise all of steps (i) to (v). In some embodiments, the trapping steps (ii) and/or (iv) may trap gas by sorption, particularly by adsorption. A sorbent material may be used, which may be selective for particular species. Desorption may be effected by heating the trap. A catalyst may be used in step (iii), which catalyses any of the reactions (a) to (e) listed above. Step (v) may be based on mass spectrometry or spectroscopy. The sample may be a solid or heavy liquid, and in particular, the sample may comprise or consist of a rock sample.

In some embodiments, all of the reacted gas is subjected to step (v). In other words, in some embodiments, the isotope ratio of each fraction is determined. In some embodiments, the apparatus does not provide any means for venting gases between the reactor and the isotope ratio spectrometer.

Further features and advantages of the invention will become apparent from the following description of embodiments of the invention, given by way of example only, which is made with reference to the accompanying drawings.

BRIEF DESCRIPTION OF THE DRAWING

FIG. 1 is a schematic representation of the gas flow path according to one embodiment of the invention.

DETAILED DESCRIPTION OF CERTAIN INVENTIVE EMBODIMENTS

The term "hydrocarbon" as used herein, includes organic compounds formed of carbon and hydrogen, optionally substituted with one or more heteroatoms including sulphur, nitrogen and oxygen. "Non-hydrocarbons" encompasses compounds that are not substantially formed of both carbon and hydrogen, and specifically includes CO, $CO_2$, $NO_x$ (particularly $NO_2$), $H_2$, $N_2$ and $SO_x$ (particularly $SO_2$).

According to one embodiment, thermogravimetric analysis of rock is completed using a Weatherford® Source Rock Analyzer (SRA) 1.

50-100 milligram-sized sample aliquots are heated under an anoxic atmosphere in a small crucible to give three initial fractions, termed herein as S1 ("volatile" hydrocarbons),
S2 ("cracked" or "pyrolyzed" hydrocarbons),
S3 ("freely desorbed" $CO_2$), and Air is then introduced to the crucible atmosphere to oxidize (combust) the remaining organic matter to yield fraction S4, containing as CO and $CO_2$ ("combustible" matter).

The SRA is a quantitative instrument and is equipped with a calibrated flame ionization detector (FID, for hydrocarbons in S1 and S2) and two calibrated infrared detectors (IRs, for detection of CO and $CO_2$ in S3 and S4). This quantitative analysis allows a qualitative (e.g. relative hydrocarbon type and degree of saturation) and semi-quantitative (e.g. total organic carbon content and maturity) assessment of the source rock.

Stable isotope data provides valuable extra data, allowing for determination of various features of the source rock, including but not limited to (a) whether the oil inventoried in the S1 fraction is genetically related to the kerogen in the S2 fraction by comparison of their $\delta^{13}C$ signatures, (b) the impact of sulphur content on kerogen-to-oil conversion kinetics via their respective sulphur content and $\delta^{34}S$ compositions, and (c) the impact of drilling mud overprinting to the S1 fraction by comparing the covariance of its $\delta^{13}C$ composition with that of S2 and aliquots of drilling mud themselves.

In one embodiment, as shown in FIG. 1, a heated transfer line 2 connects the SRA 1 output to a hydrocarbon trap 3. The transfer line is 2 a metal tube (e.g. stainless steel, copper, nickel) that is wrapped in heating tape or wound with resistive heating wire and insulated. The heated transfer line 2 is heated to a temperature of about 100-400° C. A thermocouple is connected to the tube to monitor the temperature.

The hydrocarbon trap 3 can be a thermally insulated metal (e.g. stainless steel, brass, nickel, etc.) or glass tube. A resistive heating wire is wound around the trap to allow the trap to be heated up to about 350° C. The tube is filled with a sorbent material that specifically traps hydrocarbons at a given temperature, whilst not retaining $CO_2$ or other analyte gases. The sorbent can be based on a metal oxide, a polymer, or a molecular sieve; the particle dimensions of the sorbent can range from 120 to 28 mesh. The trap temperature can be adjusted from about −180° C. to about 350° C. at a rate of up to 200° C./min, such that in use, sorbed hydrocarbons can be rapidly released in a single short burst or pulse into the reactor 4. The trap 3 outlet may be connected to the reactor 4 directly, or via another heated transfer line 2.

In an alternative embodiment, the heated transfer line 2 connects the SRA 1 output directly to the reactor 4 input (and trap 3 is not present).

The reactor 4 may comprise a quartz, nickel or alumina tube, which can be kept empty or be loaded with a catalyst. The catalyst may comprise transition and/or noble metal (e.g., copper, platinum, nickel, chromium, palladium, etc.) wires or powder, either alone or in various mixtures with each other (such as copper, nickel and platinum wires intertwined). In alternative embodiments, the reactor 4 includes a second inlet for the introduction of either an oxidizing or a reducing reagent gas to synthesize an oxidation or reducing catalyst, respectively, in situ. The reactor 4 can be heated up to 1500° C. by use of a furnace to effectuate catalytic oxidation (producing $CO_2$ and/or $SO_2$), sequential catalytic oxidation-reduction (producing $N_2$), singular catalytic reduction (producing $H_2$ and CO), or pyrolysis (producing $H_2$).

The reactor 4 outlet is coupled to a downstream gas trap 5. The coupling may be a direct connection, or may be via a heated transfer line 2. In some embodiments, a water trap may be provided in the gas flow path between the reactor 4 and the downstream gas trap 5. The downstream trap 5 is similar in structure to the hydrocarbon trap 3 described above. However, the sorbent material is selected to specifically trap CO and/or $CO_2$ and/or $SO_2$ and/or $N_2$ and/or $H_2$. In use, this traps analyte gas which can either be generated in the SRA itself, or be the result of the reactions occurring in the reactor.

The downstream gas trap 5 outlet is coupled to the isotope ratio spectrometer 6 inlet, either directly or via a heated transfer line 2. The IRS 6 may be an isotope ratio mass spectrometer (IRMS) or a spectroscopy-based system.

In embodiments, the apparatus may additionally comprise gas flow control units such as tee pieces (T-pieces) and selective valves. These can be employed to control gas flow along the gas flow path, thereby allowing precise and accurate measurements to be taken; the particular units employed and their location within the flow path will depend on their desired function, as will be apparent to the skilled person. In one example embodiment, valves are provided in the gas flow between the downstream gas trap 5 and the IRS 6, such that non-analyte gases are diverted around the IRS (i.e. out of the gas path). This advantageously prevents the IRS from being saturated (which can lead to non-linear IRS behaviour, as discussed above). In such embodiments, a helium stream may be connected to the valves, whereby when non-analyte gases are being diverted around the IRS, the helium stream passes through the IRS. This can be effected using a four-port valve, or two 3-port valves in series.

In use, a flow of volatilized hydrocarbons and non-hydrocarbon gases is evolved from a rock sample in the SRA 1. This passes into the heated transfer line 2. As described above, the apparatus may or may not contain a hydrocarbon trap 3. The hydrocarbon trap 3 (where present) is connected to the reactor 4 either directly or via an additional heated transfer line 2. If the trap 3 is in place, hydrocarbons (including those containing sulphur and nitrogen) are trapped and focused at a cool temperature, whilst all other non-hydrocarbon gases including CO and $CO_2$ pass through the trap. After a pre-defined time or event-based trigger, the trapped hydrocarbons are released into the reactor 4 by rapidly heating the trap 3 to maintain the pneumatic cohesion (i.e. narrow peak) of the desorbed sample. If the trap 3 is not in place, then the whole stream including hydrocarbons passes through the reactor 4. Oxidized and/or reduced non-hydrocarbon gaseous products then exit the reactor 4 and are trapped and concentrated on the gas trap 5. After a pre-defined time or event-based trigger, the gas trap 5 is heated releasing trapped analyte gases ($CO_2$ and/or $SO_2$ and/or $N_2$ and/or $H_2$) into the Isotope Ratio Spectrometer 6.

The above embodiments are to be understood as illustrative examples of the invention. Further embodiments of the invention are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. An apparatus comprising:
   a thermogravimetric analyzer;
   a reactor, wherein an outlet of the thermogravimetric analyzer is coupled to a reactor inlet;
   an isotope ratio spectrometer, wherein an outlet of the reactor is coupled to a spectrometer inlet;
   such that a gas flow path is provided from the thermogravimetric analyzer to the isotope ratio spectrometer,
   wherein a first selective gas trap is included in the gas flow path between the reactor and the spectrometer, and a second selective gas trap in the gas flow path between the thermogravimetric analyzer and the reactor,
   wherein each selective gas trap comprises a sorbent material that selectively and reversibly sorbs one or more gases present in a gas flow in use.

2. The apparatus of claim 1, wherein the first selective gas trap is configured to trap one or more gases selected from the group consisting of carbon monoxide, carbon dioxide, sulphur dioxide, nitrogen and hydrogen.

3. The apparatus of claim 2, wherein the first selective gas trap is configured to trap carbon dioxide.

4. The apparatus of claim 1, wherein the second selective gas trap is configured to trap hydrocarbon gases.

5. The apparatus of claim 4, wherein said hydrocarbon gases comprise hydrocarbons substituted with sulphur, oxygen, nitrogen, and combinations thereof.

6. The apparatus of claim 1, wherein the first and/or second selective gas trap additionally comprises a heater, such that the trap can be heated in use to desorb trapped gas.

7. The apparatus of claim 1, wherein the reactor comprises a catalyst, which catalyses one or more of (a) oxidation of hydrocarbons and carbon monoxide to carbon dioxide, (b) oxidation of sulphur-containing compounds to sulphur dioxide, (c) conversion of nitrogen-containing compounds to nitrogen, (d) reduction of hydrocarbons to hydrogen gas and carbon monoxide, (e) pyrolysis of hydrocarbons to hydrogen gas.

8. The apparatus of claim 1, wherein the isotope ratio spectrometer differentiates isotopes by mass spectrometry or spectroscopy.

9. A method of determining isotope ratios in fractions of a sample, the method comprising the sequential steps of;
   (i) heating the sample in a thermogravimetric analyser to thermally differentiate fractions of the sample;
   (iii) selective reaction of the step (i) output to produce a reacted gas; and
   (v) completing isotope ratio spectrometry wherein the method additionally comprises;
   (ii) selectively and reversibly trapping components of the step (i) output prior to step (iii); and/or
   (iv) selectively and reversibly trapping components of the reacted gas prior to step (v).

10. A method according to claim 9, wherein step (iii) comprises one or more of the following reactions; (a) oxidation of hydrocarbons and carbon monoxide to carbon dioxide, (b) oxidation of sulphur-containing compounds to sulphur dioxide, (c) conversion of nitrogen-containing compounds to nitrogen, (d) reduction of hydrocarbons to hydrogen gas and carbon monoxide, (e) pyrolysis of hydrocarbons to hydrogen gas.

11. A method of claim 9, wherein the sample comprises rock.

12. The method of claim 10, wherein the sample comprises rock.

* * * * *